United States Patent
Franc et al.

(10) Patent No.: US 7,767,709 B2
(45) Date of Patent: *Aug. 3, 2010

(54) PHARMACEUTICAL COMPOSITION FOR ORAL ADMINISTRATION

(75) Inventors: Ales Franc, Brno (CZ); Petr Sova, Hradec Králové (CZ)

(73) Assignee: PLIVA-Lachema a.s., Brno (CZ)

( * ) Notice: Subject to any disclaimer, the term of this patent is extended or adjusted under 35 U.S.C. 154(b) by 0 days.

This patent is subject to a terminal disclaimer.

(21) Appl. No.: 12/305,337

(22) PCT Filed: Jun. 20, 2007

(86) PCT No.: PCT/CZ2007/000058

§ 371 (c)(1), (2), (4) Date: Dec. 17, 2008

(87) PCT Pub. No.: WO2007/147371

PCT Pub. Date: Dec. 27, 2007

(65) Prior Publication Data

US 2010/0010083 A1  Jan. 14, 2010

(30) Foreign Application Priority Data

Jun. 20, 2006  (CZ) .............................. PV 2006-402

(51) Int. Cl.
*A61K 31/28* (2006.01)
(52) U.S. Cl. ...................................... 514/492; 514/489
(58) Field of Classification Search ................. 514/492, 514/489
See application file for complete search history.

(56) References Cited

U.S. PATENT DOCUMENTS

2009/0175947 A1 * 7/2009 Franc et al. ................. 424/489

2009/0209641 A1 * 8/2009 Franc et al. ................. 514/492

* cited by examiner

*Primary Examiner*—Raymond J Henley, III
(74) *Attorney, Agent, or Firm*—Notaro, Michalos & Zaccaria P.C.

(57) ABSTRACT

An oral pharmaceutical composition characterized in that it consists of a suspension of a platinum complex of general formula I, wherein A and A' independently of one another are an $NH_3$ group or an amino or diamino group containing 1 to 18 carbon atoms, B and B' independently of one another are a halogen atom or a hydroxy group or are an —O—C(O)—R or an —O—C(O)—R' group wherein R and R' independently of one another are hydrogen atom, an alkyl, alkenyl, aryl, aralkyl, alkylamino or alkoxy group which groups contain 1 to 10 carbon atoms, or functional derivatives of these groups, X and X' independently of one another are a halogen atom or a monocarboxylate group containing 1 to 20 carbon atoms, or X and X' together form a dicarboxylate group containing 2 to 20 carbon atoms, in at least one pharmaceutically acceptable vegetable, animal, mineral, synthetic or semisynthetic oil and/or in at least one pharmaceutically acceptable vegetable, animal, mineral, synthetic or semisynthetic oily substance, in which suspension the content of the platinum complex of general formula I is 0.5 to 50% by weight based on the total weight of the composition, and which suspension optionally contains at least one pharmaceutically acceptable excipient.

(I)

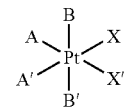

10 Claims, No Drawings

PHARMACEUTICAL COMPOSITION FOR ORAL ADMINISTRATION

FIELD OF THE INVENTION

This invention relates to a pharmaceutical composition containing a tetravalent platinum complex as active substance and enabling practically instant release and improved absorption of the active substance in oral administration.

BACKGROUND OF THE INVENTION

It is generally known that platinum complexes exhibit a broad antitumor effect which is utilized in treatment of a number of tumor diseases. So far, the therapeutic practice makes use only of complexes of bivalent platinum, especially cisplatinum, carboplatinum or oxaliplatinum. However, bivalent platinum complexes are unstable in the gastrointestinal system and/or they are very poorly absorbed. This makes the use of bivalent platinum complexes in an oral, for the patient more advantageous, dosage form impossible. It has been found that some complexes of tetravalent platinum have not this disadvantage and retain their antitumor activity even when administered orally. These complexes of tetravalent platinum were disclosed as novel chemical compounds for oral administration in EP 0 328 274, EP 0 423 707 and PCT/CZ99/00015.

However, complexes of tetravalent platinum are very sparingly soluble in water (about 0.03 g/100 ml), low bulk density (about 0.2 g/ml), low tap density (about 0.4 g/ml), and a high electrostatic charge. The said physical properties represent an important problem for the preparation of a solid oral drug form. Moreover, complexes of tetravalent platinum are chemically unstable in contact with metals or with many currently used excipients. These problems have been solved with partial success in PCT/CZ99/00015 which patent document describes the preparation of solid drug forms of specific tetravalent platinum complexes in the form of inclusion complexes of cyclodextrins with the said tetravalent platinum complexes. According to the mentioned patent document, these inclusion complexes are obtained by reaction of cyclodextrins with complexes of tetravalent platinum in an organic solvent and subsequent lyophilization, and are used for oral application. However, the employed amount of cyclodextrin markedly limits the content of the tetravalent platinum complex present in the oral drug form, which is a disadvantage. The obtained oral drug form thus has a relatively large volume and is difficult to swallow, making a single-dose oral application of higher doses of tetravalent platinum complex impossible.

From what has been said above, it is evident that there is still a need for an oral drug form containing complexes of tetravalent platinum, which drug form would be stable and have a sufficiently high content of the tetravalent platinum complex. To provide such a drug form is the aim of the present invention.

SUMMARY OF THE INVENTION

The above mentioned goal has been achieved by an oral pharmaceutical composition characterized in that it consists of a suspension of a platinum complex of general formula I,

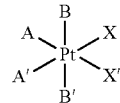

(I)

wherein
A and A' independently of one another are an $NH_3$ group or an amino or diamino group containing 1 to 18 carbon atoms,
B and B' independently of one another are a halogen atom or a hydroxy group or are an —O—C(O)—R or an —O—C(O)—R' group wherein R and R' independently of one another are hydrogen atom, an alkyl, alkenyl, aryl, aralkyl, alkylamino or alkoxy group which groups contain 1 to 10 carbon atoms, or functional derivatives of these groups,
X and X' independently of one another are a halogen atom or a monocarboxylate group containing 1 to 20 carbon atoms, or X and X' together form a dicarboxylate group containing 2 to 20 carbon atoms,
in at least one pharmaceutically acceptable vegetable, animal, mineral, synthetic or semisynthetic oil and/or in at least one pharmaceutically acceptable vegetable, animal, mineral, synthetic or semisynthetic oily substance, in which suspension the content of the platinum complex of general formula I is 0.5 to 50% by weight based on the total weight of the composition, and which suspension optionally contains at least one pharmaceutically acceptable excipient.

Preferably, the content of the platinum complex of general formula I in the pharmaceutical composition amounts to 10 to 40% by weight, based on the total weight of the composition.

A pharmaceutically acceptable oil in the pharmaceutical composition may be preferably sunflower oil, corn oil, rape oil, arachis oil, peanut oil, sesame oil, linseed oil, olive oil, castor oil and/or a mineral oil, and/or a pharmaceutically acceptable oily substance in the pharmaceutical composition may advantageously be synthetic or semisynthetic oily substances, e.g. esters of glycerol with higher aliphatic acids, known under trade marks Akomed, Labrafac, Miglyol and Softisan, and propylene glycol laurate known under trade mark Lauroglycol.

Preferably, 100% of particles of platinum complex of general formula I in the pharmaceutical composition are of size smaller than 100 µm, preferably smaller than 40 µm, particularly smaller than 10 µm.

The above mentioned suspension of platinum complex of general formula I is advantageously enclosed in hard gelatin or hydroxypropyl methyl cellulose capsules or in soft gelatin capsules or pearls. Preferably, one capsule contains 50 to 350 mg of the platinum complex of general formula I.

The pharmaceutical composition in the form of capsules is advantageously obtained in a capsulating machine in which the surfaces in contact with the suspension of the platinum complex of general formula I are inert toward this suspension.

The invention also relates to the above mentioned pharmaceutical composition as a drug for the therapy of tumor diseases.

The term "oily substance" as used herein denotes a substance which, although terminologically not explicitly designated as oil, exhibits characteristic properties of oils.

Within the framework of the invention it has been surprisingly found that by formulating a platinum complex of general formula I in the form of suspension in the defined oils and/or oily substances it is unexpectedly possible to achieve all the properties desired for an oral drug form of the said complex. The formation of suspension of the platinum complex eliminates its low density as well as its extremely high electrostatic charge, and even enables an optional, from the point of biological accessibility advantageous, wet micronization of the platinum complex, which would be practically impossible to achieve in the dry, untreated state. Moreover, the use of external liquid phase in suspension of the platinum complex enables application of liquid emulsifiers that entirely or at least partially emulgate the external phase of the suspension into the outer hydrophilic phase of the digestive tract, and optionally application of penetration promoters that further increase the biological accessibility of the platinum complex from the pharmaceutical composition according to the invention. In the case of platinum complexes of general formula I which dissolve with great difficulty in the medium of gastrointestinal tract, this also leads to an enhanced dissolution and absorption of the platinum complex as the result of decrease of interfacial tension. The oleophilic nature of the oily phase, in which the platinum complex of general formula I is suspended and in which medium this complex is to a substantial extent absorbed, protects the platinum complex against the aggressive action of hydrophilic gastric juice in the digestive tract.

With a content of the platinum complex of general formula I equal to 0.5 to 50% by weight, the suspension of the platinum complex of general formula I can be disintegrated as well as filled without any risk.

Optionally, in addition to the platinum complex of general formula I and an oil and/or an oily substance, a pharmaceutical composition according to the invention may contain pharmaceutically acceptable excipients generally used in compositions of this type. As such excipients one may use particularly surfactants, i.e. substances with emulgating properties for systems of the type oil/water, such as esters of sorbitane with polyoxyethylene known under the trade mark Tween, esters of sorbitane with higher aliphatic acids known under the trade mark Span, polyoxyethylene glycerol esters of higher aliphatic acids, known under the trade marks Targat S and Targat L, polyoxyethylene ethers of higher aliphatic alcohols known under the trade marks Cremophor and Brij, and glycerol stearates known under the trade marks Arlaton and Arlacel.

Further one may mention penetration promotors such as propylene glycol monocaprylate known under the trade mark Capryol, semisynthetic glycerides on the basis of hydrogenated vegetable oil known under the trade mark Gelucire, glycerol monostearate known under the trade mark Inwitor, polyoxyethylated glycerides of oleic acid known under the trade mark Labrafil, polyglycerol esters of oleic acid known under the trade mark Plurol Oleique, copolymers of ethylene oxide and propylene oxide known under the trade marks Poloxamer and Synperonic, a mixture of pegylated mono- and diglycerides known under the trade mark Softigen, and polyethylene glycol caprate, polyethylene glycol laurate and polyethylene glycol stearate known under the trade mark PEG-32, as well as mixtures of these surfactants in any ratio.

It is also possible to introduce stabilizers such as common antioxidants of the type tocopherol, ascorbyl palmitate, propyl gallate, butylhydroxyanisol, butylhydroxytoluene and nordihydroxyguaiarethane, employed in usual concentrations.

In the following part, the invention will be explained in more detail using specific examples of execution which are of illustrative value only and do not limit in any way the scope of the invention that is unequivocally defined by the appending Claims.

In these examples, as a specific representative of platinum complex of general formula I serves the (OC-6-43)-bis(acetato)-(1-adamantylamine)-ammine-dichloroplatinum(IV) complex of code name LA-12 and of structural formula II:

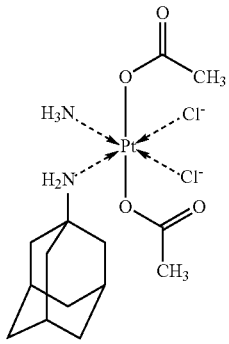

(II)

In the Examples, this specific platinum complex is denoted by its code name.

EXAMPLES

Example 1

Method of Preparing Hard Gelatin Capsules

Platinum complex LA-12 (1 part by weight) is suspended in arachis oil (oleum arachidis) (4 parts by weight). The obtained suspension is milled in a ball mill to obtain a suspension in which 100% of particles of the platinum complex LA-12 are of size smaller than 40 µm, whereupon the suspension is filled into hard gelatin capsules so that the content of the platinum complex LA-12 in each capsule is 200 mg. The amount of the suspension in each capsule is thus 1000 mg.

Example 2

Method of Preparing Hard Gelatin Capsules

Platinum complex LA-12 (1 part by weight) is milled in a ball mill in the presence of arachis oil (4 parts by weight) and emulsifier Tween 60 (0.1 part by weight) to obtain a suspension in which 100% of particles of the platinum complex LA-12 are of size smaller than 40 µm, whereupon the obtained suspension is filled into hard gelatin capsules so that the content of the platinum complex LA-12 in each capsule is 200 mg. The amount of the suspension in each capsule is thus 1020 mg.

Example 3

Method of Preparing Hard Gelatin Capsules

Platinum complex LA-12 (1 part by weight) is suspended in a mixture of glycerol ester Labrafac (4 parts by weight), semisynthetic glyceride Gelucire 44/14 (0.1 part by weight) and emulsifier Tween 60 (0.1 part by weight) and the obtained suspension is milled in a ball mill to obtain a suspension in which 100 % of particles of the platinum complex LA-12 are of size smaller than 40 µm, whereupon the suspension is filled into hard gelatin capsules so that the content of the platinum complex LA-12 in each capsule is 200 mg. The amount of the suspension in each capsule is thus 1040 mg.

The invention claimed is:

1. A pharmaceutical composition for oral administration, characterized in that it consists of a suspension of a platinum complex of structural formula II:

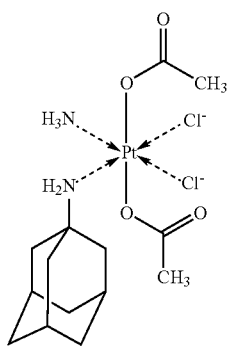

in at least one pharmaceutically acceptable vegetable, animal, mineral, synthetic or semisynthetic oil and/or in at least one pharmaceutically acceptable vegetable, animal, mineral, synthetic or semisynthetic oily substance, in which suspension the content of platinum complex of formula II is 0.5 to 50% by weight based on the total weight of the composition, and which suspension optionally contains at least one pharmaceutically acceptable excipient.

2. The pharmaceutical composition according to claim 1, characterized in that the content of the platinum complex of formula II in the suspension of the platinum complex of formula II is 10 to 40% by weight, based on the total weight of the composition.

3. The pharmaceutical composition according to claim 1, characterized in that as a pharmaceutically acceptable oil it contains sunflower oil, corn oil, rape oil, arachis oil, peanut oil, sesame oil, linseed oil, olive oil, castor oil and/or a mineral oil, and/or as a pharmaceutically acceptable oily substance it contains synthetic or semisynthetic oily substances, e.g. esters of glycerol with higher aliphatic acids and propylene glycol laurate.

4. The pharmaceutical composition according to claim 1, characterized in that 100% of particles of the platinum complex of formula II are of size smaller than 100 µm.

5. The pharmaceutical composition according to claim 4, characterized in that 100% of particles of the platinum complex of formula II are of size smaller than 40 µm.

6. The pharmaceutical composition according to claim 5, characterized in that 100% of particles of the platinum complex formula II are of size smaller than 10 µm.

7. The pharmaceutical composition according to claim 1, characterized in that it is enclosed in hard gelatin or hydroxypropyl methyl cellulose capsules or in soft gelatin capsules or pearls.

8. The pharmaceutical composition according to claim 7, characterized in that one capsule contains 50 to 350 mg of the platinum complex of formula II.

9. The pharmaceutical composition according to claim 7, characterized in that it is enclosed in a capsule and is obtained using a capsulating machine whose surfaces coming into contact with the suspension of the platinum complex of formula II are inert towards this suspension.

10. The pharmaceutical composition according to claim 1, as a drug for the treatment of tumor diseases.

* * * * *